(12) United States Patent
Allard et al.

(10) Patent No.: US 9,463,148 B2
(45) Date of Patent: *Oct. 11, 2016

(54) FOAM DYE COMPOSITION COMPRISING A POLYCONDENSATE OF ETHYLENE OXIDE AND PROPYLENE OXIDE

(71) Applicant: L'OREAL, Paris (FR)

(72) Inventors: Delphine Allard, Paris (FR); Caroline Goget, Summit, NJ (US); Richard Sabourin, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/348,295

(22) PCT Filed: Sep. 28, 2012

(86) PCT No.: PCT/EP2012/069209
§ 371 (c)(1),
(2) Date: Mar. 28, 2014

(87) PCT Pub. No.: WO2013/045626
PCT Pub. Date: Apr. 4, 2013

(65) Prior Publication Data
US 2014/0237736 A1    Aug. 28, 2014

Related U.S. Application Data

(60) Provisional application No. 61/548,320, filed on Oct. 18, 2011.

(30) Foreign Application Priority Data

Sep. 30, 2011    (FR) ...................................... 11 58836

(51) Int. Cl.
| | | |
|---|---|---|
| *A61Q 5/10* | (2006.01) | |
| *A61K 8/41* | (2006.01) | |
| *A61K 8/86* | (2006.01) | |
| *A61K 8/90* | (2006.01) | |
| *A61K 8/04* | (2006.01) | |
| *A61K 8/19* | (2006.01) | |
| *A45D 19/02* | (2006.01) | |
| *A45D 19/00* | (2006.01) | |

(52) U.S. Cl.
CPC .............. *A61K 8/415* (2013.01); *A45D 19/02* (2013.01); *A61K 8/046* (2013.01); *A61K 8/19* (2013.01); *A61K 8/41* (2013.01); *A61K 8/411* (2013.01); *A61K 8/86* (2013.01); *A61K 8/90* (2013.01); *A61Q 5/10* (2013.01); *A45D 2019/0066* (2013.01)

(58) Field of Classification Search
CPC ...... A61K 8/411; A61K 8/415; A45D 19/02; A45D 2019/0066
USPC ............................................ 8/405, 406, 477
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 3,206,462 A | 9/1965 | McCarty |
| 3,709,437 A | 1/1973 | Wright |
| 3,874,870 A | 4/1975 | Green et al. |
| 3,912,808 A | 10/1975 | Sokol |
| 3,929,990 A | 12/1975 | Green et al. |
| 3,937,364 A | 2/1976 | Wright |
| 3,966,904 A | 6/1976 | Green et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,022,351 A | 5/1977 | Wright |
| 4,025,617 A | 5/1977 | Green et al. |
| 4,025,627 A | 5/1977 | Green et al. |

(Continued)

FOREIGN PATENT DOCUMENTS

| | | |
|---|---|---|
| CA | 1069522 A1 | 1/1980 |
| DE | 2359399 A1 | 6/1975 |

(Continued)

OTHER PUBLICATIONS

STIC Search Report dated Nov. 21, 2014.*
Co-pending U.S. Appl. No. 14/348,225, "Foam Dye Composition Comprising at Least One Particular Oxyethylenated Nonionic Surfactant," Inventors: Gautier Deconinck et al., Filed: Mar. 28, 2014, (National State Appln. of PCT/EP2012/069213).
Co-pending U.S. Appl. No. 14/348,212, "Foam Dye Composition Comprising at Least One Liquid Fatty Alcohol and a Particular Cationic Polymer," Inventors: Caroline Goget et al., Filed: Mar. 28, 2014, (National Stage Appln. of PCT/EP2012/069215).

(Continued)

*Primary Examiner* — Eisa Elhilo
(74) *Attorney, Agent, or Firm* — The Marbury Law Group, PLLC

(57) ABSTRACT

The invention relates to a composition for dyeing human keratin fibers such as the hair, in foam form, comprising at least one alkaline agent, at least one oxidizing agent, at least one oxidation dye precursor and at least one polycondensate of ethylene oxide and of propylene oxide of structure (I) below: H—(O—CH$_2$—CH$_2$)$_a$(O—CH(CH$_3$)—CH$_2$)$_b$—(O—CH$_2$—CH$_2$)$_{a'}$—OH, in which a, a' range from 2 to 150, and b ranges from 1 to 100. The invention also relates to a process for dyeing human keratin fibers using this composition. A subject of the invention is also a device for dyeing keratin fibers, comprising the composition of the invention in liquid form and a foam dispenser for delivering the composition in the form of a foam.

16 Claims, No Drawings

(56) References Cited

U.S. PATENT DOCUMENTS

| | | |
|---|---|---|
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,075,136 A | 2/1978 | Schaper |
| 4,137,180 A | 1/1979 | Naik et al. |
| 4,147,306 A | 4/1979 | Bennett |
| 4,166,894 A | 9/1979 | Schaper |
| RE30,199 E | 1/1980 | Rose et al. |
| 4,184,615 A | 1/1980 | Wright |
| 4,197,865 A | 4/1980 | Jacquet et al. |
| 4,217,914 A | 8/1980 | Jacquet et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,579,732 A | 4/1986 | Grollier et al. |
| 4,598,862 A | 7/1986 | Rice |
| 4,608,250 A | 8/1986 | Jacquet et al. |
| 4,615,467 A | 10/1986 | Grogan et al. |
| 4,777,040 A | 10/1988 | Grollier et al. |
| 4,874,554 A | 10/1989 | Lange et al. |
| 4,948,579 A | 8/1990 | Jacquet et al. |
| 4,970,066 A | 11/1990 | Grollier et al. |
| 5,061,289 A | 10/1991 | Clausen et al. |
| 5,196,189 A | 3/1993 | Jacquet et al. |
| 5,364,031 A | 11/1994 | Taniguchi et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,692,539 B2 | 2/2004 | Desenne et al. |
| 6,730,789 B1 | 5/2004 | Birault et al. |
| 7,799,746 B2 | 9/2010 | Patel et al. |
| 8,298,296 B2 | 10/2012 | Wood et al. |
| 2001/0037531 A1 | 11/2001 | Lorenz |
| 2002/0050013 A1 | 5/2002 | Vidal et al. |
| 2003/0019051 A9 | 1/2003 | Vidal et al. |
| 2003/0172473 A1 | 9/2003 | Desenne et al. |
| 2004/0098815 A1 | 5/2004 | Schmenger et al. |
| 2005/0226838 A1* | 10/2005 | Krause et al. ............ 424/70.13 |
| 2010/0154136 A1 | 6/2010 | Hercouet et al. |
| 2010/0236570 A1 | 9/2010 | Fujinuma et al. |
| 2011/0073128 A1 | 3/2011 | Ogawa et al. |
| 2011/0284421 A1 | 11/2011 | Lane et al. |
| 2011/0284586 A1* | 11/2011 | Kerr et al. ..................... 222/190 |
| 2014/0013521 A1* | 1/2014 | Goget et al. ..................... 8/410 |

FOREIGN PATENT DOCUMENTS

| | | |
|---|---|---|
| DE | 3843892 A1 | 6/1990 |
| DE | 4133957 A1 | 4/1993 |
| DE | 19543988 A1 | 5/1997 |
| EP | 0122324 A1 | 10/1984 |
| EP | 0548620 A1 | 6/1993 |
| EP | 1321128 A2 | 11/1996 |
| EP | 0770375 A1 | 5/1997 |
| EP | 2204157 A1 | 7/2010 |
| EP | 2204160 A1 | 7/2010 |
| EP | 2283803 A1 | 2/2011 |
| FR | 2080759 A | 11/1971 |
| FR | 2190406 A2 | 2/1974 |
| FR | 2270846 A1 | 12/1975 |
| FR | 2316271 A1 | 1/1977 |
| FR | 2320330 A1 | 3/1977 |
| FR | 2336434 A1 | 7/1977 |
| FR | 2413907 A1 | 8/1979 |
| FR | 2733749 A1 | 11/1996 |
| FR | 2801308 | 5/2001 |
| FR | 2833832 A1 | 5/2003 |
| FR | 2886136 A1 | 12/2006 |
| GB | 1026975 | 4/1966 |
| GB | 1026978 | 4/1966 |
| GB | 1153196 | 5/1969 |
| GB | 1546809 A | 5/1979 |
| JP | 219576 | 1/1990 |
| JP | 5163124 | 6/1993 |
| WO | 9408969 A1 | 4/1994 |
| WO | 9408970 A1 | 4/1994 |
| WO | 9615765 A1 | 5/1996 |

OTHER PUBLICATIONS

International Search Report for PCT/EP2012/069213, (Nov. 2012).
International Search Report for PCT/EP2012/069215, (Nov. 2012).
International Search Report for PCT/EP2012/069209, (Nov. 2012).
Edens, M.W., et al., "Applications of Block Copolymer Surfactants," Developments in Block Copolymer Science and Technology, Wiley, U.S., Jan. 1, 2004, pp. 326-340.
English Abstract for EP 0548620, (Jun. 1993).
English Abstract for EP 0770375, (May 1997).
English Abstract for EP 1321128, (Nov. 1996).
English Abstract for EP 1728500, (Dec. 2006).
English Abstract for JP219576, (Jan. 1990).
English Abstract for JP 5163124, (Jun. 1993).
Mintel: "Mousse Hair Colourant," GNPD, Sep. 21, 2010, XP002644135, 2pgs.
Mintel: "Foam Color," GNPD, Oct. 14, 2009 XP002643790, 2pgs.
Non-Final Office Action for co-pending U.S. Appl. No. 14/348,212, dated Aug. 14, 2014.
Non-Final Office Action for co-pending U.S. Appl. No. 14/348,225, dated Sep. 26, 2014.
Final Office Action for co-pending U.S. Appl. No. 14/348,212, dated Mar. 26, 2015.

* cited by examiner

FOAM DYE COMPOSITION COMPRISING A POLYCONDENSATE OF ETHYLENE OXIDE AND PROPYLENE OXIDE

This is a national stage application of PCT/EP2012/069209, filed internationally on Sep. 28, 2012, which claims priority to U.S. Provisional Application No. 61/548,320, filed on Oct. 18, 2011, as well as French Application No. 1158836, filed on Sep. 30, 2011, all of which are incorporated herein by reference in their entireties.

The present invention relates to a composition in foam form comprising dye precursors.

Among the methods for dyeing human keratin fibres, such as the hair, mention may be made of oxidation dyeing or permanent dyeing. More particularly, this form of dyeing uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds which, when combined with oxidizing products, can give access to coloured entities.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colors to be obtained.

Permanent dyeing processes thus consist in using, with the dye composition, an aqueous composition comprising at least one oxidizing agent, such as hydrogen peroxide, under alkaline pH conditions in the vast majority of cases. The alkaline agent conventionally used is aqueous ammonia or other alkaline agents, such as alkanolamines.

Dye compositions may take various forms such as lotions, gels, emulsions, creams or foams. Dyeing foams are pleasant to use, however they often exhibit a poor staying power over time. For example, it is possible to observe a rapid disappearance of the foam after application or a non-uniform application along the fibres.

There is a real need to develop oxidation dye compositions in foam form that are easy to prepare and to apply, and which remain sufficiently stable over time while retaining efficient dyeing properties.

This aim and others are achieved by the present invention, one subject of which is thus a composition for dyeing keratin fibres such as the hair, in foam form, comprising at least one alkaline agent, at least one oxidizing agent, at least one oxidation dye precursor and at least one polycondensate of ethylene oxide and of propylene oxide of structure (I) below

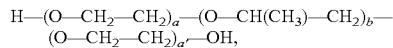

in which a, a' range from 2 to 150, and b ranges from 1 to 100.

The invention also relates to a process for dyeing human keratin fibres using this composition.

A subject of the invention is similarly a multi-compartment device comprising, in a first compartment, a first composition containing at least one oxidation dye precursor, at least one alkaline agent and at least one polycondensate of structure (I); in a second compartment, a second composition containing one or more oxidizing agents, one of the two compartments being equipped with a component for delivering the composition of the invention in foam form after mixing with the other composition, or the component for delivering the composition in foam form is included in a third compartment.

A subject of the invention is also a device for dyeing keratin fibres, comprising the composition of the invention in liquid form and a foam dispenser for delivering the composition in the form of a foam.

The composition of the invention is in the form of a foam that is particularly pleasant to apply. It has a light, airy texture, which makes it particularly pleasant to use. The qualities of the foam are sufficiently long-lasting to enable uniform application of the dye product, without running. The composition of the invention makes it possible to obtain improved dyeing properties, such as strength of the colour, resistance to external agents (shampooing, perspiration, light) and selectivity, which are particularly efficient.

Other features and advantages of the invention will become more clearly apparent on reading the description and the examples that follow.

In the text hereinbelow, unless otherwise indicated, the limits of a range of values are included in that range. The expression "at least one" is equivalent to the expression "one or more".

The composition according to the invention contains at least one polycondensate of ethylene oxide and propylene oxide of structure (I) defined above (polyethylene glycol/polypropylene glycol/polyethylene glycol triblock). In the chemical structure described above, preferably, a and a' range from 10 to 130 and b ranges from 20 to 80, better still a and a' range from 50 to 130 and b ranges from 30 to 80, and even better still a and a' range from 80 to 130 and b ranges from 40 to 80. According to one particular embodiment, a and a' are identical.

The polycondensate of ethylene oxide and propylene oxide that is useful in the composition of the invention preferably has a weight-average molecular weight ranging from 250 to 19 000, better still ranging from 1200 to 15 000, in particular ranging from 1500 to 10 000 and even better still ranging from 1500 to 5000.

Advantageously, the polycondensate of ethylene oxide and propylene oxide has a cloud point, at 10 g/l in distilled water, greater than or equal to 20° C. and preferably greater than or equal to 60° C. The cloud point is measured according to standard ISO 1065.

As polycondensate products of ethylene oxide and propylene oxide that may be used according to the invention, mention may be made of the polyethylene glycol/polypropylene glycol/polyethylene glycol triblock polycondensate products sold under the name Synperonic, for instance Synperonic® PE/F32 (INCI name: Poloxamer 108), Synperonic® PE/F108 (INCI name: Poloxamer 338), Synperonic® PE/L44 (INCI name: Poloxamer 124), Synperonic® PE/L42 (INCI name: Poloxamer 122), Synperonic® PE/F127 (INCI name: Poloxamer 407), Synperonic® PE/F88 (INCI name: Poloxamer 238), Synperonic® PE/L64 (INCI name: Poloxamer 184), Synperonic® PE/F88 (INCI name: Poloxamer 238), Synperonic® PE/F87 (INCI name: Poloxamer 237) by the company Croda, or Lutrol® F68 (INCI name: Poloxamer 188) by the company BASF.

According to one embodiment of the invention, the amount of the polycondensate(s) of ethylene oxide and propylene oxide preferably ranges from 0.1% to 20% by weight, even more preferentially from 0.5% to 10% by weight and better still from 0.7% to 5% by weight relative to the total weight of the composition.

The foam composition according to the invention comprises at least one alkaline agent. This agent may be chosen from mineral or organic or hybrid alkaline agents, or mixtures thereof.

The mineral alkaline agent(s) are preferably chosen from aqueous ammonia, alkali carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a $pK_b$ at 25° C. of less than 12, preferably less than 10 and even more advantageously less than 6. It should be noted that it is the $pK_b$ corresponding to the function of highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds of formula (II) below:

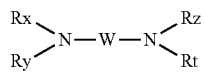

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (II') below:

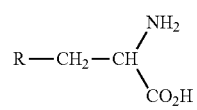

in which R denotes a group chosen from:

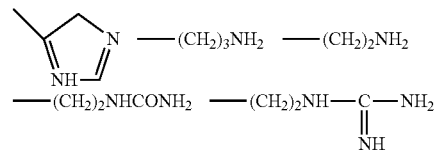

The compounds corresponding to formula (II') are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that can be used in the present invention, mention may be made especially of carnosine, anserine and baleine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Mention may be made in particular of the use of guanidine carbonate or monoethanolamine hydrochloride as hybrid compounds.

According to one particular embodiment, the composition of the invention comprises, as alkaline agent, one or more alkanolamines.

Preferably, the alkanolamine is monoethanolamine.

In one variant of the invention, the composition of the invention comprises, as alkaline agent, one or more alkanolamines, preferably monoethanolamine, and aqueous ammonia. In this variant, the alkanolamine(s) are present in a predominant amount relative to the aqueous ammonia, the content of the latter being expressed as ammonia.

Advantageously, the composition according to the invention has a content of alkaline agent(s) ranging from 0.01% to 30% by weight, preferably from 0.1% to 20% by weight and better still from 1% to 10% by weight relative to the weight of the said composition.

The composition according to the invention also comprises at least one oxidizing agent.

The oxidizing agents are chosen, for example, from hydrogen peroxide, urea peroxide, alkali metal bromates or ferricyanides, peroxygenated salts, for instance persulfates, perborates, peracids and precursors thereof and percarbonates of alkali metals or of alkaline-earth metals. Advantageously, the oxidizing agent is hydrogen peroxide.

The content of oxidizing agent(s) more particularly represents from 0.1% to 20% by weight and preferably from 0.5% to 10% by weight relative to the weight of the composition.

As indicated previously, the composition according to the invention comprises one or more oxidation dye precursors.

Oxidation bases and couplers may be used as oxidation dye precursors.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases, mention may be made, by way of example, of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases of use in the present invention are the 3-aminopyrazolo[1,5-a]pyridine oxidation bases or the addition salts thereof described, for example, in Patent Application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and addition salts thereof.

Among the pyrimidine derivatives that may be mentioned are the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethypamino-1-methylpyrazole, and the addition salts thereof. Use may also be made of 4,5-diamino-1-(β-methoxyethyl) pyrazole.

Use will preferably be made of a 4,5-diaminopyrazole and more preferably still of 4,5-diamino-1-(β-hydroxyethyl) pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used.

As heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

Among the couplers that may be used in the composition of the invention, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The addition salts of the oxidation bases and couplers are especially chosen from the addition salts with an acid such as the hydrochlorides, hydrobromides, sulfates, citrates, succinates, tartrates, lactates, tosylates, benzenesulfonates, phosphates and acetates.

The oxidation base(s) are each generally present in an amount of from 0.0001% to 10% by weight relative to the total weight of the composition, and preferably from 0.005% to 5% by weight relative to the total weight of the composition.

The coupler(s) each generally represent from 0.0001% to 10% by weight relative to the total weight of the composition, and preferably from 0.005% to 5% by weight relative to the total weight of the composition.

The composition according to the invention may contain synthetic or natural, cationic or nonionic, direct dyes.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures. In particular, mention may be made of direct dyes from among: azo; methine; carbonyl; azine; nitro (hetero)aryl; tri(hetero)arylmethane; porphyrin; phthalocyanine and natural direct dyes, alone or as mixtures.

When they are present, the direct dye(s) more particularly represent(s) from 0.0001% to 10% by weight and preferably from 0.005% to 5% by weight of the total weight of the composition.

The composition according to the invention may comprise one or more additional surfactants other than the polycondensates of formula (I). These additional surfactants may be cationic, amphoteric, nonionic and/or anionic surfactants. The additional surfactants are surfactants known per se in the field of dyeing keratin fibres.

The amphoteric or zwitterionic surfactant(s) that may be used in the present invention may especially be optionally quaternized secondary or tertiary aliphatic amine derivatives, in which the aliphatic group is a linear or branched chain containing from 8 to 22 carbon atoms, the said amine derivatives containing at least one anionic group, for instance a carboxylate, sulfonate, sulfate, phosphate or phosphonate group. In particular, mention may be made of $(C_8-C_{20})$alkylbetaines, sulfobetaines, $(C_8-C_{20}$ alkyl)amido$(C_3-C_8$ alkyl)betaines or $(C_8-C_{20}$ alkyl)amido$(C_6-C_8$ alkyl) sulfobetaines. Among the optionally quaternized, secondary or tertiary aliphatic amine derivatives that can be used, as defined above, mention may also be made of the compounds having the respective structures (III) and (III') below:

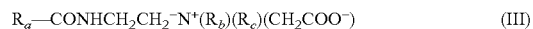

$$R_a\text{—CONHCH}_2\text{CH}_2\text{—N}^+(R_b)(R_c)(CH_2COO^-) \quad (III)$$

in which:

$R_a$ represents a $C_{10}$-$C_{30}$ alkyl or alkenyl group derived from an acid, $R_a$—COOH, preferably present in hydrolysed coconut oil, represents a heptyl, nonyl or undecyl group, $R_b$ represents a β-hydroxyethyl group, and $R_c$ represents a carboxymethyl group;

and

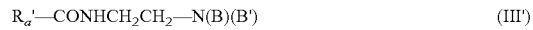

$$R_a'\text{—CONHCH}_2\text{CH}_2\text{—N(B)(B')} \quad (III')$$

in which:

B represents —CH$_2$CH$_2$OX',

B' represents —(CH$_2$)$_z$—Y', with z=1 or 2,

X' represents the group —CH$_2$—COOH, CH$_2$—COOZ', —CH$_2$CH$_2$—COOH, —CH$_2$CH$_2$—COOZ', or a hydrogen atom, Y' represents —COOH, —COOZ', the group —CH$_2$—CHOH—SO$_3$H or —CH$_2$—CHOH—SO$_3$Z', Z' represents an ion derived from an alkali metal or alkaline-earth metal, such as sodium, an ammonium ion or an ion derived from an organic amine, $R_a'$ represents a $C_{10}$-$C_{30}$ alkyl or alkenyl group of an acid $R_a'$—COOH preferably present in coconut oil or in hydrolysed linseed oil, an alkyl group, especially a $C_{17}$ alkyl group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of betaines comprising at least one saturated or unsaturated, $C_8$-$C_{30}$ fatty chain, and in particular the compounds of formula (A):

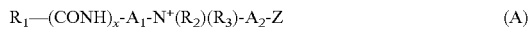

$$R_1-(CONH)_x-A_1-N^+(R_2)(R_3)-A_2-Z \quad (A)$$

with
x denoting 0 or 1,
$A_1$ and $A_2$ denoting, independently of one another, a linear or branched $C_1$-$C_{10}$ alkylene radical optionally substituted with a hydroxyl radical,
$R_1$ denoting a linear or branched $C_6$-$C_{30}$ alkyl or alkenyl radical,
$R_2$ and $R_3$ denoting, independently of one another, a linear or branched $C_1$-$C_4$ alkyl radical,
Z denoting a $CO_2^-$ group or an $SO_3^-$ group.

Preferably, $R_2$ and $R_3$ denote a methyl radical.

The amphoteric surfactant(s) of betaine type used in the cosmetic composition according to the present invention may especially be ($C_{8-20}$)alkylbetaines, ($C_{8-20}$)alkylsulfobetaines, ($C_{8-20}$ alkyl)amido($C_{2-8}$ alkyl)betaines or ($C_{8-20}$ alkyl)amido($C_{6-8}$ alkyl)sulfobetaines.

Among the amphoteric surfactants mentioned above that are preferably used are ($C_{8-20}$ alkyl)betaines and ($C_{8-20}$ alkyl)amido($C_{2-8}$ alkyl)betaines, and mixtures thereof.

More particularly, the amphoteric surfactants of betaine type are selected from cocobetaine and cocamidopropylbetaine.

The term "anionic surfactant" means a surfactant comprising, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2$, $HPO_2^-$, $PO_2^-$, POH, $PO^-$.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, alpha-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside citrates, $C_6$-$C_{24}$ alkyl polyglycoside tartrates and $C_6$-$C_{24}$ alkyl polyglycoside sulfosuccinates.

When the anionic surfactant(s) are in salt form, they may be chosen from alkali metal salts such as the sodium or potassium salt and preferably the sodium salt, the ammonium salts, the amine salts and in particular the amino alcohol salts or the alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Among the anionic surfactants, it is preferred, according to the invention, to use alkyl sulfate salts and alkyl ether sulfate salts and mixtures thereof.

The term "cationic surfactant" means a surfactant that is positively charged when it is contained in the composition according to the invention. This surfactant may bear one or more positive permanent charges or may contain one or more cationizable functions within the composition according to the invention.

The cationic surfactant(s) that may be used according to the present invention are preferably chosen from optionally polyoxyalkylenated primary, secondary or tertiary fatty amines, or the salts thereof, quaternary ammonium salts, and mixtures thereof.

The fatty amines generally comprise at least one $C_8$-$C_{30}$ hydrocarbon-based chain. Among the fatty amines that can be used according to the invention, examples that may be mentioned include stearylamidopropyldimethylamine and distearylamine.

Examples of quaternary ammonium salts that may especially be mentioned include:
those corresponding to the general formula (IV) below:

$$\begin{bmatrix} R_8 & R_{10} \\ & N \\ R_9 & R_{11} \end{bmatrix}^+ X^- \quad (IV)$$

in which the groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ denoting a group containing from 8 to 30 carbon atoms, preferably from 12 to 24 carbon atoms. The aliphatic groups may comprise heteroatoms such as, in particular, oxygen, nitrogen, sulfur and halogens. The aliphatic groups are chosen, for example, from $C_{1-30}$ alkyl, $C_{1-30}$ alkoxy, polyoxy($C_2$-$C_6$)alkylene, $C_{1-30}$ alkylamide, ($C_{12}$-$C_{22}$)alkylamido($C_2$-$C_6$)alkyl, ($C_{12}$-$C_{22}$)alkylacetate and $C_{1-30}$ hydroxyalkyl; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylaryl-sulfonates.

Among the quaternary ammonium salts of formula (IV), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is particularly preferred to use the chloride salts of these compounds;

quaternary ammonium salts of imidazoline, for instance those of formula (V) below:

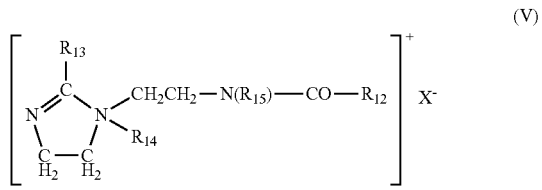
(V)

in which $R_{12}$ represents an alkyl or alkenyl group containing from 8 to 30 carbon atoms, derived for example from tallow fatty acids, $R_{13}$ represents a hydrogen atom, a $C_1$-$C_4$ alkyl group or an alkyl or alkenyl group containing from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion selected from the group consisting of halides, phosphates, acetates, lactates, alkyl sulfates, alkylsulfonates or alkylarylsulfonates in which the alkyl and aryl groups each preferably comprise from 1 to 20 carbon atoms and from 6 to 30 carbon atoms. $R_{12}$ and $R_{13}$ preferably denote a mixture of alkyl or alkenyl groups comprising from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary diammonium or triammonium salts, in particular of formula (VI):

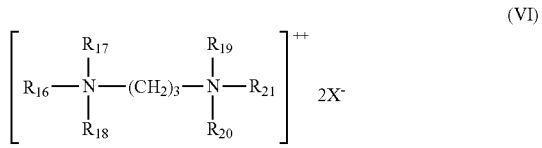
(VI)

in which $R_{16}$ denotes an alkyl radical containing approximately from 16 to 30 carbon atoms, which is optionally hydroxylated and/or interrupted by one or more oxygen atoms, $R_{17}$ is selected from hydrogen and an alkyl radical containing from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which are identical or different, are selected from hydrogen and an alkyl radical containing from 1 to 4 carbon atoms, and $X^-$ is an anion selected from the group of halides, acetates, phosphates, nitrates and methyl sulfates. Such compounds are, for example, Finquat CT-P, available from the company Finetex (Quaternium 89), and Finquat CT, available from the company Finetex (Quaternium 75), quaternary ammonium salts containing at least one ester function, such as those of formula (VII) below:

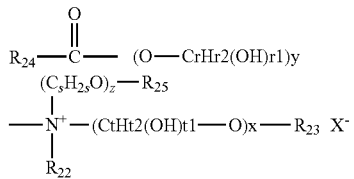
(VII)

in which:
$R_{22}$ is selected from $C_1$-$C_6$ alkyl groups and $C_1$-$C_6$ hydroxyalkyl or dihydroxyalkyl groups;
$R_{23}$ is selected from:
the group

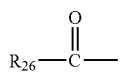

groups $R_{27}$, which are linear or branched, saturated or unsaturated $C_1$-$C_{22}$ hydrocarbon-based groups,
a hydrogen atom,
$R_{25}$ is selected from:
the group

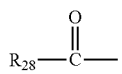

groups $R_{29}$, which are linear or branched, saturated or unsaturated $C_1$-$C_6$ hydrocarbon-based groups,
a hydrogen atom,
$R_{24}$, $R_{26}$ and $R_{28}$, which are identical or different, are selected from linear or branched, saturated or unsaturated $C_7$-$C_{21}$ hydrocarbon radicals;
r, s and t, which may be identical or different, are integers ranging from 2 to 6;
r1 and t1, which may be identical or different, are equal to 0 or 1,
and r2+r1=2r and t1+t2=2t,
y is an integer ranging from 1 to 10;
x and z, which may be identical or different, are integers ranging from 0 to 10;
$X^-$ is a simple or complex, organic or inorganic anion;
with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and may have 12 to 22 carbon atoms, or may be short and may have from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

y is advantageously equal to 1.

Preferably, r, s and t, which may be identical or different, equal 2 or 3, and even more particularly are equal to 2.

The anion $X^-$ is preferably a halide (chloride, bromide or iodide) or an alkyl sulfate, more particularly methyl sulfate. However, it is possible to use methanesulfonate, phosphate, nitrate, tosylate, an anion derived from an organic acid, such as acetate or lactate, or any other anion that is compatible with the ammonium containing an ester function.

The anion $X^-$ is even more particularly chloride or methyl sulfate.

Use is made more particularly, in the composition according to the invention, of the ammonium salts of formula (VII) in which:

$R^{22}$ denotes a methyl or ethyl group, x and y are equal to 1;

z is equal to 0 or 1;

r, s and t are equal to 2;

$R_{23}$ is selected from:

the group

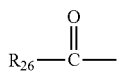

methyl, ethyl or $C_{14}$-$C_{22}$ hydrocarbon-based groups, a hydrogen atom, $R_{25}$ is selected from:

the group

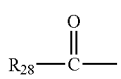

a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

The hydrocarbon-based groups are advantageously linear.

Mention may be made, for example, of the compounds of formula (VII) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, of triisopropanolamine, of an alkyldiethanolamine or of an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably a dimethyl or diethyl sulfate), methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in patents U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the quaternary ammonium salts containing at least one ester function, which can be used, it is preferred to use dipalmitoylethylhydroxyethylmethylammonium salts.

The additional nonionic surfactants are more particularly chosen from mono-oxyalkylenated or polyoxyalkylenated and monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitol, saturated or unsaturated, oxyethylenated plant oils, The surfactants contain a number of moles of ethylene oxide and/or of propylene oxide of between 1 and 100, preferably between 2 and 50 and preferably between 2 and 30.

In accordance with one preferred embodiment of the invention, the oxyalkylenated nonionic surfactants are chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

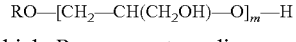

in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Nonionic surfactants that may also be mentioned include non-oxyethylenated fatty acid esters of sorbitan, fatty acid esters of sucrose, optionally oxyalkylenated alkylpolyglycosides, alkylglucoside esters, derivatives of N-alkylglucamine and of N-acylmethylglucamine, aldobionamides and amine oxides.

According to one embodiment, the composition of the invention comprises one or more additional nonionic or anionic surfactants. Preferentially, the composition of the invention comprises one or more additional nonionic surfactants.

The total content of additional surfactants in the composition of the invention is in general from 0.1% to 30% by weight, preferably from 1% to 20% by weight and better still from 1% to 10% by weight, relative to the weight of the composition.

The composition may also contain various adjuvants conventionally used in compositions for dyeing or lightening the hair, such as anionic polymers, cationic polymers, and nonionic polymers, or mixtures thereof; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of the composition.

Preferentially, the composition according to the invention comprises one or more cationic polymers.

The composition according to the invention may comprise water and/or one or more organic solvents.

Examples of organic solvents that may be mentioned include linear or branched and preferably saturated monoalcohols or diols, comprising 2 to 10 carbon atoms, such as ethanol, isopropanol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol monomethyl, monoethyl or monobutyl ether, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The organic solvents, when they are present, generally represent between 1% and 40% by weight relative to the total weight of the dye composition, and preferably between 5% and 30% by weight relative to the total weight of the dye composition.

The composition is preferably aqueous. In this case, it preferably comprises from 30% to 95% by weight of water, better still from 40% to 90% by weight of water and even better still from 50% to 85% by weight of water relative to the total weight of the composition.

The pH of the composition according to the invention, if it is aqueous, is generally between 3 and 12, preferably between 5 and 11 and preferentially between 7 and 11, limits inclusive.

It may be adjusted to the desired value by means of acidifying or basifying agents usually used in the dyeing of keratin fibres, and in particular the aforementioned alkaline agents of the invention.

The composition, before dispersing in the form of a foam, may result from the mixing of two or more than two compositions.

The composition according to the invention is, on application to the keratin fibres, in the form of a foam.

The composition in foam form according to the invention is formed from a mixture of air or an inert gas with the composition described previously.

According to one particularly preferred embodiment, the composition according to the invention is in the form of a temporary foam produced just before use.

According to this embodiment, the composition may be packaged in a foam dispenser. They may either be products known as "aerosols" dispensed from a pressurized container with the aid of a propellant gas and thus forming a foam at the moment they are dispensed, or compositions dispensed from a container using a mechanical pump connected to a dispensing head, the passage of the composition into the dispensing head converting it into a foam at the latest at the outlet orifice of such a head.

The propellant gas that may be used may be chosen from carbon dioxide, nitrogen, nitrogen oxide, dimethyl ether, volatile hydrocarbons such as butane, isobutane, propane and pentane, and mixtures thereof.

The dispensing head is such that the substance that is sprayed in foam form is the composition according to the invention, i.e. the mixture of the composition with the oxidizing agent(s) and the composition with the oxidation dye precursor(s).

According to another embodiment, the composition may be in a foam dispenser of "pump-action bottle" type. These dispensers comprise a dispensing head for delivering the composition, a pump and a dip tube for transferring the composition from the container into the head in order to deliver the product. The foam is formed by forcing the composition to pass through a material comprising a porous substance such as a sintered material, a filtering grid made of plastic or of metal, or similar structures.

Such dispensers are well known to those skilled in the art and are described in patents: U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.), and U.S. Pat. No. 5,364,031 (Tamiguchi et al.).

In practice, for this variant, the oxidizing agent(s) are packaged in a first container equipped with a closure, and the oxidation dye precursor(s) are packaged in a second container, different from the first, and also closed by a closing member. The closing member may be a pump-dispensing mechanism. The composition according to the invention is then formed by mixing, before use, a composition with the oxidizing agent(s) and a composition with the oxidation dye precursor(s). To this end, to limit the number of containers provided, one from among the first and second container defines an internal volume that is sufficient to receive therein all of the two compositions. The mixture of the compositions may be homogenized by closing this container and by shaking the container. The closure of the container is advantageously carried out directly with the dispensing head. This dispensing head comprises a mechanical pump held in a ring intended for mounting by snap-fitting or screwing onto the neck of the container containing the mixture. The pump comprises a pump body connected to a dip tube to enable the whole of the mixture to be dispensed. The pump also comprises a push button for activation of the pump body, such that, on each activation, a dose of composition is sucked inside the dip tube and ejected in foam form out of the dispensing orifice of the head.

The containers are preferentially made of a thermoplastic material, and obtained via extrusion blow-moulding or injection blow-moulding processes. In particular, the container for conditioning the composition with the oxidation dye precursor(s) may be made (to be reported in other projects) of a material comprising a non-zero proportion of EVOH. The pump is, for example, the standard "F2-L9" model offered by the company Rexam. According to this preferred embodiment, one subject of the invention is a non-aerosol device comprising the composition of the invention.

The dyeing process according to the invention consists in applying the composition according to the invention to wet or dry human keratin fibres over a time sufficient to develop the desired coloration. According to the invention, the composition applied to the keratin fibres is in foam form. The dyeing process is generally performed at room temperature (between 15 and 25° C.) and up to temperatures that may be as high as 60° C. to 80° C.

After a leave-on time of from one minute to one hour and preferably from 5 minutes to 30 minutes, the human keratin fibres are rinsed with water, and optionally washed with a shampoo and then rinsed with water.

The examples that follow serve to illustrate the invention without, however, being limiting in nature.

EXAMPLES

The following compositions are prepared (the amounts are expressed in g % of active material):

| Ingredients | Amount (g) |
| --- | --- |
| Ammonium thiolactate | 0.2 |
| Aqueous ammonia (expressed as NH$_3$) | 0.8 |
| Erythorbic acid | 0.1 |
| Monoethanolamine | 2 |
| Ethylenediaminetetraacetic acid | 0.1 |
| Oleyl alcohol | 0.5 |
| Fragrance | 0.4 |
| Polydimethyldiallylammonium chloride (Polyquaternium-6) | 0.5 |
| Hexylene glycol (2-methyl-2,4-pentanediol) | 2 |
| Dipropylene glycol | 2 |
| 96° ethyl alcohol | 3 |
| Propylene glycol | 2 |
| Oxyethylenated decyl alcohol (3 OE) | 4 |
| Protected oxyethylenated (4 OE) rapeseed acid amide (INCI: PEG-4 rapeseed amide) | 3 |
| Lauryl ether carboxylic acid (4.5 OE) | 2 |
| Glyceryl C12 alkyl ether (1.5 mol) (INCI: glyceryl lauryl ether) | 3 |
| Condensate of ethylene oxide and of propylene oxide and ethylene oxide (MW: 14000) (128 OE/54 OP/128 OE) (INCI: Poloxamer 338) | 1 |
| Hydrogen peroxide | 4.5 |
| Phosphoric acid | qs |
| Etidronic acid, tetrasodium salt | 0.04 |
| Tetrasodium pyrophosphate | 0.02 |
| Sodium salicylate | 0.02 |
| Glycerol | 2 |

-continued

| Ingredients | Amount (g) |
| --- | --- |
| Laureth-11 | 1 |
| 1,4-Diaminobenzene | 0.8 |
| 1-β-Hydroxyethyloxy-2,4-diaminobenzene dihydrochloride | 0.04 |
| 1N,N-Bis(2-hydroxyethyl)amino-4-aminobenzene sulfate monohydrate | 0.18 |
| 2-Methyl-1,3-dihydroxybenzene | 0.028 |
| 1,3-Dihydroxybenzene | 0.68 |
| 1-Hydroxy-3-aminobenzene | 0.24 |
| Water | qs 100 |

The above dye composition is obtained by mixing, before use, the following two compositions in a composition A/composition B weight ratio of 0.666.

| Composition A | % by weight |
| --- | --- |
| Ammonium thiolactate | 0.5 |
| Aqueous ammonia (expressed as NH$_3$) | 2 |
| Erythorbic acid | 0.25 |
| Monoethanolamine | 5 |
| Ethylenediaminetetraacetic acid | 0.25 |
| Oleyl alcohol | 1.25 |
| Fragrance | 1 |
| Polydimethyldiallylammonium chloride (Polyquaternium-6) | 1.25 |
| Hexylene glycol (2-methyl-2,4-pentanediol) | 5 |
| Dipropylene glycol | 5 |
| 96° ethyl alcohol | 7.5 |
| Propylene glycol | 5 |
| Oxyethylenated decyl alcohol (3 OE) | 10 |
| Protected oxyethylenated (4 OE) rapeseed acid amide (INCI: PEG-4 rapeseed amide) | 7.5 |
| Lauryl ether carboxylic acid (4.5 OE) | 5 |
| Glyceryl C12 alkyl ether (1.5 mol) (INCI: glyceryl lauryl ether) | 7.5 |
| Condensate of ethylene oxide and of propylene oxide and ethylene oxide (MW: 14000) (128 OE/54 OP/128 OE) (INCI: Poloxamer 338) | 2.5 |
| 1,4-Diaminobenzene | 2 |
| 1-β-Hydroxyethyloxy-2,4-diaminobenzene dihydrochloride | 0.1 |
| 1N,N-Bis(2-hydroxyethyl)amino-4-aminobenzene sulfate monohydrate | 0.45 |
| 2-Methyl-1,3-dihydroxybenzene | 0.07 |
| 1,3-Dihydroxybenzene | 1.7 |
| 1-Hydroxy-3-aminobenzene | 0.6 |
| Water | qs 100 |

| Composition B | % by weight |
| --- | --- |
| Glycerol | 4 |
| Etidronic acid, tetrasodium salt | 0.06 |
| Tetrasodium pyrophosphate | 0.04 |
| Sodium salicylate | 0.035 |
| Hydrogen peroxide | 7.5 |
| Laureth-11 | 1 |
| Phosphoric acid | qs pH 2.2 |
| Water | qs 100 |

The mixture is introduced in an amount of 65 g (26 g of composition A+39 g of composition B) into a pump bottle (Rexam L9 equipped with a dip tube). The device produces a compact foam on pumping. This compact foam is applied to natural or permanent-waved grey hair containing 90% white hairs, without disintegrating immediately on application. The comfort on application is very good. After a leave-in time of 30 minutes, the locks are rinsed, washed with a standard 10 shampoo, rinsed again and then dried, to give a dark chestnut-brown coloration. This coloration is strong and sparingly selective.

The invention claimed is:

1. A foam dye composition comprising at least one oxidation dye precursor, at least one oxidizing agent, at least one alkaline agent, and at least one polycondensate of ethylene oxide and of propylene oxide of formula (I):

(I)

wherein a and a', which may be identical or different, range from 50 to 130, and b ranges from 30 to 80.

2. The foam dye composition according to claim 1, wherein the at least one oxidation dye precursor comprises at least one oxidation base chosen from para-phenylenediamines, bis(phenyl)alkylenediamines, para-aminophenols, ortho-aminophenols and heterocyclic bases, and the addition salts thereof, and optionally at least one coupler chosen from meta-phenylenediamines, meta-aminophenols, meta-diphenols, naphthalene-based couplers and heterocyclic couplers, and the addition salts thereof.

3. The foam dye composition according to claim 1, wherein a and a', which may be identical or different, range from 80 to 130 and b ranges from 40 to 80.

4. The foam dye composition according to claim 1, wherein a and a' are identical.

5. The foam dye composition according to claim 1, wherein the at least one polycondensate of ethylene oxide and propylene oxide is present in an amount ranging from about 0.1% to about 20% by weight, relative to the total weight of the composition.

6. The foam dye composition according to claim 5, wherein the at least one polycondensate of ethylene oxide and propylene oxide is present in an amount ranging from about 0.7% to about 5% by weight, relative to the total weight of the composition.

7. The foam dye composition according claim 1, wherein the at least one oxidizing agent is hydrogen peroxide.

8. The foam dye composition according to claim 1, wherein the at least one alkaline agent is chosen from mineral alkaline agents and organic alkaline agents.

9. The foam dye composition according to claim 1, wherein the at least one alkaline agent is chosen from ammonia and monoethanolamine, and mixtures thereof.

10. The foam dye composition according to claim 1, further comprising at least one surfactant chosen from anionic and nonionic surfactants.

11. The foam dye composition according to claim 10, wherein the at least one surfactant is chosen from nonionic surfactants.

12. The foam dye composition according to claim 1, wherein the composition is packaged in an aerosol device comprising a means for generating a foam.

13. The foam dye composition according to claim 1, wherein the composition is packaged in liquid form in a non-aerosol device comprising a container equipped with a mechanical pumping system and a dispensing system for delivering the composition in the form of a foam.

14. The foam dye composition according to claim 1, wherein the composition is packaged in liquid form in a non-aerosol device comprising a container equipped with a mechanical pumping system and a dispensing system for delivering the composition in the form of a foam.

15. A hair dyeing process comprising:
(a) mixing at least one oxidizing agent with a composition comprising at least one dye precursor, at least one alkaline agent, and at least one polycondensate of ethylene oxide and of propylene oxide of formula (I):

(I)

wherein a and a', which may be identical or different, range from 50 to 130, and b ranges from 30 to 80, and
(b) applying the mixture in the form of a foam to the hair.

16. A multi-compartment device comprising:
a first compartment containing a first composition comprising at least one oxidation dye precursor, at least one alkaline agent and at least one polycondensate of formula (I);

(I)

wherein a and a', which may be identical or different, range from 2 to 150, and b ranges from 1 to 100, and
a second compartment containing a second composition comprising at least one oxidizing agent,
wherein one of the first and second compartments optionally comprises a component for delivering a mixture of the first composition and the second composition in the form of a foam,
and further wherein when neither of the first or second compartments is equipped with a component for delivering the mixture in the form of a foam, the device comprises a third compartment comprising a component for delivering the mixture in the form of a foam.

* * * * *